United States Patent [19]
Lake et al.

[11] Patent Number: 5,698,493
[45] Date of Patent: Dec. 16, 1997

[54] SYNERGISTIC HERBICIDAL COMPOSITION AND METHOD OF USE THEREOF

[75] Inventors: Byron H. Lake, Novato, Calif.; Trevor J. Purnell, Farnham, England

[73] Assignee: Zeneca Limited, London, England

[21] Appl. No.: 710,824

[22] Filed: Sep. 23, 1996

Related U.S. Application Data

[63] Continuation of Ser. No. 231,219, Apr. 22, 1994, abandoned.
[51] Int. Cl.$^6$ .................... A01N 43/70; A01N 33/22
[52] U.S. Cl. .................................................. 504/133
[58] Field of Search ...................................... 504/133

[56] References Cited

U.S. PATENT DOCUMENTS

| | | | |
|---|---|---|---|
| 4,759,794 | 7/1988 | Hsu | 71/93 |
| 4,937,386 | 6/1990 | Ueda et al. | 568/31 |
| 4,997,473 | 3/1991 | Nguyen | 71/98 |
| 5,006,158 | 4/1991 | Carter et al. | 71/98 |
| 5,089,046 | 2/1992 | Lee et al. | 71/103 |

FOREIGN PATENT DOCUMENTS

| | | |
|---|---|---|
| 0 186 118 | 7/1986 | European Pat. Off. |
| 0 230 596 | 8/1987 | European Pat. Off. |
| 0 336 898 | 10/1989 | European Pat. Off. |
| 354047 | 2/1990 | European Pat. Off. |
| 2 675 340 | 10/1992 | France |
| 92/19107 | 11/1992 | WIPO |

OTHER PUBLICATIONS

Chemical Abstracts, vol. 109, No. 1, Jul. 4, 1988, Columbus, Ohio, US; Abstract No. 2362; F. E. Katz et al., "Weed Control in corn with new experimental herbicides"; and Proc. Annu. Meet. Northest. Weed Sc. Soc., vol. 42, 1988, pp. 3–5.

Chemical Abstracts, vol. 115, No. 3, Jul. 22, 1991, Columbus, Ohio, US; Abstract No. 24261; J. S. Wilson et al., "Weed control in no–tillage and conventional corn (Zea mays) with ICI–A 0051 and SC–0774"; and Weed Technol., vol. 4, No. 4, 1990, pp. 731–738.

Herbicide Handbook of the Weed Science Society of America, 5th Edition, 1983, pp. 30–34.

Primary Examiner—S. Mark Clardy
Attorney, Agent, or Firm—Melissa A. Shaw

[57] ABSTRACT

A synergistic herbicidal composition comprising atrazine and either NMSC (i.e., 2-(2'-nitro-4'-methylsulfonylbenzoyl)-1,3-cyclohexanedione), or NMSOC (i.e., 2-(2'-nitro-4'-methylsulfonyloxybenzoyl)-1,3-cyclohexanedione):

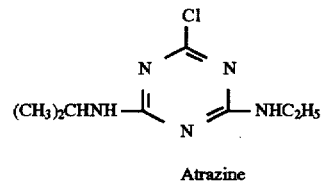

Atrazine

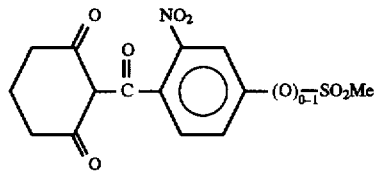

NMSC/NMSOC

Also disclosed is a method of controlling undesirable vegetation by applying an effective amount of such composition to the locus of the vegetation to be controlled.

9 Claims, No Drawings

SYNERGISTIC HERBICIDAL COMPOSITION AND METHOD OF USE THEREOF

This application is a continuation of application Ser. No. 08/231,219, filed Apr. 22, 1994, abandoned.

FIELD OF THE INVENTION

In one aspect the present invention is directed to a synergistic herbicidal composition comprising (a) 2-(2'-nitro-4'-methylsulfonylbenzoyl)-1,3-cyclohexanedione or 2-(2'-nitro-4'-methylsulfonyloxybenzoyl)-1,3-cyclohexanedione; and (b) 2-chloro-4-ethylamino-6-isopropylamino-S-triazine. In another aspect, the present invention is directed to a method of controlling the growth of undesirable vegetation by applying an herbicidally effective amount of such synergistic composition to the locus of such vegetation.

BACKGROUND OF THE INVENTION

The protection of crops from weeds and other vegetation which inhibit crop growth is a constantly recurring problem in agriculture. To help combat this problem, researchers in the field of synthetic chemistry have produced an extensive variety of chemicals and chemical formulations effective in the control of such unwanted growth. Chemical herbicides of many types have been disclosed in the literature and a large number are in commercial use.

In some cases, active herbicides have been shown to be more effective in combination than when applied individually. The result is often termed "synergism", since the combination demonstrates a potency or activity level exceeding that which it would be expected to have, based on a knowledge of the individual potencies of the components. The present invention resides in the discovery that certain cyclohexanediones and 2-chloro-4-ethylamino-6-isopropylamino-S-triazine(atrazine), already known individually for their herbicidal potency, display a synergistic effect when applied in combination.

The compounds forming the combination which is the subject of the present invention are independently known in the art for their effects on plant growth. Thus, 2-chloro-4-ethylamino-6'-isopropylamino-S-triazine, commonly known as atrazine, is commercially sold under various trade names, and is described in the Herbicide Handbook of the Weed Science Society of America, 5th Edition, 1983; 2-(2'-nitro-4'-methylsulfonylbenzoyl)-1,3-cyclohexanedione is disclosed in U.S. Pat. No. 5,006,158 to Carter et al; and 2-(2'-nitro-4'-methylsulfonyloxybenzoyl-1,3-cyclohexanedione is disclosed in U.S. Pat. No. 5,089,046 to Lee et al.

DESCRIPTION OF THE INVENTION

In one aspect, the present invention is directed to a synergistic herbicidal composition comprising (a) 2-(2'-nitro-4'-methylsulfonylbenzoyl)-1,3-cyclohexanedione ("NMSC") or 2-(2'-nitro-4'-methylsulfonyloxybenzoyl)-1,3-cyclohexanedione ("NMSOC"); and (b) 2-chloro-4-ethylamino-6-isopropylamino-S-triazine.

In another aspect, this invention is directed to a method of controlling undesirable vegetation applying to the locus of such vegetation a synergistic composition comprising (a) 2-(2'-nitro-4'-methylsulfonylbenzoyl)-1,3-cyclohexanedione or 2-(2'-nitro-4'-methylsulfonyloxybenzoyl)-1,3-cyclohexanedione; and (b) 2-chloro-4-ethylamino-6-isopropylamino-S-triazine.

The terms "synergism" and "synergistic" are used herein to convey the result observed when a combination of herbicides demonstrates a potency in excess of that which the combination would be expected to produce based upon the potencies of each herbicide applied separately.

The term "herbicide" is used herein to denote a compound which controls or modifies the growth of plants. The term "herbicidally effective amount" is used to indicate the quantity of such a compound or combination of such compounds which is capable of producing a controlling or modifying effect. Controlling or modifying effects include all deviations from natural development, for example: killing, retardation, leaf burn, albinism, dwarfing and the like. The term "plants" refers to all physical parts of a plant, including seeds, seedlings, saplings, roots, tubers, stems, stalks, foliage and fruits.

In the compositions of this invention, the weight ratio of component (a) to component (b) at which the herbicidal response is synergistic, lies within the range of between about 1:50 and about 1:1, and is preferably between about 1:40 and about 4:5.

Application rates will depend upon the particular plant species and degree of control desired. In general, the compositions of the invention are most efficiently employed at a rate of 0.001 to 5 pounds per acre (0.001 to 5 kilograms per hectare).

The compositions of this invention are useful as herbicides, demonstrating synergistic activity for the control of undesirable vegetation. The compositions can be formulated in the same manner in which herbicides are generally formulated. The compounds may be applied either separately or combined as part of a two-part herbicidal system.

The object of the formulation is to apply the compositions to the locus where control is desired by a convenient method. The "locus" is intended to include soil, seeds, and seedlings, as well as established vegetation.

The composition employed in the practice of the present invention can be applied in a variety of ways known to those skilled in the art, at various concentrations. The composition is useful in controlling the growth of undesirable vegetation by pre-emergence or post-emergence application to the locus where control is desired. In practice, the composition is applied as a formulation containing the various adjuvants and carriers known to or used in the industry for facilitating dispersion. The choice of formulation and mode of application for any given compound may affect its activity, and selection will be made accordingly. The compositions of the invention may thus be formulated as granules, as wettable powders, as emulsifiable concentrates, as powders or dusts, as flowables, as solutions, suspensions or emulsions, or in controlled-release forms such as microcapsules. These formulations may contain as little as about 0.5% to as much as amount 95% or more by weight of active ingredient. The optimum amount for any given compound will depend upon the nature of the seeds or plants to be controlled.

Wettable powders are in the form of finely divided particles which disperse readily in water or other liquid carriers. The particles contain the active ingredient retained in a solid matrix. Typical solid matrices include fuller's earth, kaolin clays, silicas and other readily wet organic or inorganic solids. Wettable powders normally contain about 5% to about 95% of the active ingredient plus a small amount of wetting, dispersing, or emulsifying agent.

Emulsifiable concentrates are homogeneous liquid compositions dispersible in water or other liquid, and may consist entirely of the active compound with a liquid or solid emulsifying agent, or may also contain a liquid carrier, such as xylene, heavy aromatic naphthas, isophorone and other non-volatile organic solvents. In use, these concentrates are dispersed in water or other liquid and normally applied as a spray to the area to be treated. The amount of active ingredient may range from about 0.5% to about 95% of the concentrate.

Granular formulations include both extrudates and relatively coarse particles, and are usually applied without dilution to the area in which suppression of vegetation is desired. Typical carriers for granular formulations include sand, fuller's earth, attapulgite clay, bentonite clays, montmorillonite clay, vermiculite, perlite and other organic or inorganic materials which absorb or which can be coated with the active compound. Granular formulations normally contain about 5% to about 25% active ingredients which may include surface-active agents such as heavy aromatic naphthas, kerosene and other petroleum fractions, or vegetable oils; and/or stickers such as dextrins, glue or synthetic resins.

Dusts are free-flowing admixtures of the active ingredient with finely divided solids such as talc, clays, flours and other organic and inorganic solids which act as dispersants and carriers.

Microcapsules are typically droplets or granules of the active material enclosed in an inert porous shell which allows escape of the enclosed material to the surroundings at controlled rates. Encapsulated droplet are typically about 1 to 50 microns in diameter. The enclosed liquid typically constitutes about 50 to 95% of the weight of the capsule, and may include solvent in addition to the active compound. Encapsulated granules are generally porous granules with porous membranes sealing the granule pore openings, retaining the active species in liquid form inside the granule pores. Granules typically range from 1 millimeter to 1 centimeter, preferably 1 to 2 millimeters in diameter. Granules are formed by extrusion, agglomeration or prilling, or are naturally occurring. Examples of such materials are vermiculite, sintered clay, kaolin, attapulgite clay, sawdust and granular carbon. Shell or membrane materials include natural and synthetic rubbers, cellulosic materials, styrene-butadiene copolymers, polyacrylonitriles, polyacrylates, polyesters, polyamides, polyureas, polyurethanes and starch xanthates.

Other useful formulations for herbicidal applications include simple solutions of the active ingredient in a solvent in which it is completely soluble at the desired concentration, such as acetone, alkylated naphthalenes, xylene and other organic solvents. Pressurized sprayers, wherein the active ingredient is dispersed in finely-divided form as a result of vaporization of a low boiling dispersant solvent carrier may also be used.

Many of these formulations include wetting, dispersing or emulsifying agents. Examples are alkyl and alkylaryl sulfonates and sulfates and their salts; polyhydric alcohols; polyethoxylated alcohols; esters and fatty amines. These agents when used normally comprise from 0.1% to 15% by weight of the formulation.

Each of the above formulations can be prepared as a package containing the herbicide together with other ingredients of the formulation (diluents, emulsifiers, surfactants etc.). The formulations can also be prepared by a tank mix method, in which the ingredients are obtained separately and combined at the grower site.

These formulations can be applied to the areas where control is desired by conventional methods. Dust and liquid compositions, for example, can be applied by the use of power-dusters, boom and hand sprayers and spray dusters. The formulations can also be applied from airplanes as a dust or a spray or by rope wick applications. To modify or control growth of germinating seeds or emerging seedlings, dust and liquid formulations can be distributed in the soil to a depth of at least one-half inch below the soil surface or applied to the soil surface only, by spraying or sprinkling. The formulations can also be applied by addition to irrigation water. This permits penetration of the formulations into the soil together with the irrigation water. Dust compositions, granular compositions or liquid formulations applied to the surface of the soil can be distributed below the surface of the soil by conventional means such as discing, dragging or mixing operations.

EXAMPLES

The following Examples are intended to further illustrate the present invention and are not intended to limit the scope of this invention in any manner whatsoever.

In all three of the following examples, test plots were compared to untreated plots and rated visually in terms of percent control ranging from 0% to 100%, with 0% representing no injury to the plant species and 100% representing complete kill of all plants. All types of plant injury were taken into consideration.

The observed results from the herbicide treatments on each species for Examples I, II and III are shown in TABLES I, II and III, respectively. The observed ratings for the individual herbicide treatments are listed along with the expected ("E") and observed ("O") results from the mixtures of NMSC and atrazine. The expected results were derived from the control data using Limpel's formula (Limpel et al., 1962, "Weed Control by Dimethylchloroterephthalate Alone and in Certain Combinations", Proc. NEWCC., Vol. 16:48–53:

$$E = X + Y - \frac{XY}{100}$$

where X=observed percent injury when one of the herbicides is used alone, and

Y=observed percent injury when the other herbicide is used alone.

Example I

In Holambra, Brazil, plots were planted with the following weed species: *Echinochloa crus-galli* ("ECHCG"); *Brachiaria plantaginea* ("BRAPL"); *Digitaria ciliaris* ("DIGAD"); *Cenchrus echinatus* ("CCHEC"); *Euphorbia heterophylla* ("EPHHL"); *Bidens pilosa* ("BIDPI"); *Sida rhumbifolia* ("SIDRH") and *Amaranthus retroflexus* ("AMARE"). When such weeds reached the 3–5 leaf stage, they were treated with NMSC; atrazine; or NMSC+atrazine, at the rates indicated in Table I. Injury to the species in each plot was rated twenty-eight days after treatment. The results of such testing, as the mean of two replications, are summarized in TABLE I.

TABLE I

| | ECHCG | BRAPL | DIGAD | CCHEC | EPHHL | BIDPI | SIDRH | AMARE | IPUAO |
|---|---|---|---|---|---|---|---|---|---|
| NMSC* | | | | | | | | | |
| 18 | 0 | 0 | 3 | 0 | 42 | 53 | 47 | 33 | 23 |
| 35 | 23 | 0 | 0 | 5 | 43 | 57 | 72 | 45 | 35 |
| 70 | 30 | 8 | 20 | 0 | 47 | 69 | 82 | 50 | 53 |
| 140 | 45 | 13 | 52 | 3 | 60 | 91 | 99 | 72 | 67 |
| Atrazine* | | | | | | | | | |
| 250 | 0 | 0 | 0 | 0 | 30 | 30 | 10 | 23 | 18 |
| 500 | 0 | 0 | 0 | 13 | 47 | 45 | 30 | 40 | 33 |

| | ECHCG | | BRAPL | | DIGAD | | CCHEC | | EPHHL | | BIDPI | | SIDRH | | AMARE | | IPUAO | |
|---|---|---|---|---|---|---|---|---|---|---|---|---|---|---|---|---|---|---|
| NMSC + Atr* | E | O | E | O | E | O | E | O | E | O | E | O | E | O | E | O | E | O |
| 18 + 250 | 0 | 13 | 0 | 0 | 3 | 23 | 0 | 0 | 59 | 62 | 67 | 80 | 52 | 88 | 48 | 91 | 37 | 64 |
| 35 + 250 | 23 | 33 | 0 | 13 | 0 | 20 | 5 | 8 | 60 | 58 | 70 | 91 | 75 | 98 | 58 | 89 | 47 | 68 |
| 70 + 250 | 30 | 45 | 8 | 12 | 20 | 33 | 0 | 12 | 63 | 67 | 78 | 100 | 84 | 100 | 61 | 93 | 61 | 79 |
| 140 + 250 | 45 | 91 | 13 | 32 | 52 | 72 | 3 | 13 | 72 | 80 | 94 | 100 | 99 | 100 | 88 | 100 | 73 | 90 |
| 18 + 500 | 0 | 27 | 0 | 3 | 3 | 13 | 13 | 12 | 69 | 53 | 74 | 90 | 63 | 97 | 60 | 92 | 48 | 65 |
| 35 + 500 | 23 | 57 | 0 | 13 | 0 | 18 | 17 | 7 | 70 | 71 | 76 | 100 | 80 | 99 | 67 | 95 | 55 | 82 |
| 70 + 500 | 30 | 67 | 8 | 12 | 20 | 40 | 13 | 7 | 72 | 69 | 83 | 100 | 87 | 100 | 70 | 100 | 69 | 95 |
| 140 + 500 | 45 | 92 | 13 | 40 | 52 | 63 | 16 | 13 | 79 | 90 | 95 | 100 | 99 | 100 | 83 | 97 | 78 | 98 |

*Application rates in grams per hectare.

Example II

Near Vienna, Austria, plots were planted with seeds of the following species: *Amaranthus retroflexus* ("AMARE"); *Chenopoduim album* ("CHEAL"); *Chenopoduim hybruim* ("CHEAL") and *Datura stramonum* ("DATST"). When such plants reached the 3-5 leaf stage, they were treated with NMSC alone; atrazine alone; or NMSC+atrazine, at the rates indicated in Table II.

Thirty-five days after such application, the treated plants were compared to untreated plants. The results of such testing, as the mean of 3 replications, along with the results expected using the Limpel Formula, are summarized below in Table II.

TABLE II

| | AMARE | | AMACH | |
|---|---|---|---|---|
| NMSC Alone* | | | | |
| 12.5 | 52 | | 47 | |
| 25 | 65 | | 63 | |
| 50 | 80 | | 80 | |
| 100 | 87 | | 83 | |
| 200 | 98 | | 97 | |
| Atrazine Alone* | | | | |
| 250 | 20 | | 18 | |
| 500 | 58 | | 53 | |
| NMSC + Atrazine* | E | O | E | O |
| 12.5 + 250 | 62 | 85 | 57 | 85 |
| 25 + 250 | 72 | 96 | 70 | 95 |
| 50 + 250 | 84 | 99 | 84 | 99 |
| 100 + 250 | 90 | 99 | 86 | 98 |
| 200 + 250 | 98 | 100 | 98 | 100 |
| 12.5 + 500 | 80 | 98 | 75 | 98 |
| 25 + 500 | 85 | 99 | 83 | 98 |
| 50 + 500 | 92 | 98 | 91 | 98 |
| 100 + 500 | 95 | 99 | 92 | 99 |
| 200 + 500 | 99 | 100 | 99 | 100 |

*Application rates in grams per hectare.

Due to essentially complete control of CHEAL, CHEHY and DATST by NMSC and/or atrazine alone, little or no evidence of synergy was observed with respect to these species.

Example III

In plots located in Illinois, Iowa, Indiana, Kansas, Minnesota, South Dakota and Missouri (three replications each), seeds of the following weed species occurred: *Xanthuim strumarium* ("XANST"); *Setaria faberi* ("SETFA"); *Abutilon theophrasti* ("ABUTH"); *Chenopodium album* ("CHEAL"); *Polygonum pensylvanicum* ("POLPY"), *Solanium ptycanthum* ("SOLPT"); *Amaranthus retroflexus* ("AMARE"); and/or *Polygonum persicaria* ("POLPE"). The plots were treated with NMSC alone; atrazine alone; or NMSC+atrazine, at the rates indicated in Table III.

The results of each treatment (as a mean of the replications and location) along with the expected results from the Limpel formula are presented below in Table III.

TABLE III

| NMSC | atrazine | XANST % control observed and expected, by location | | | | SETFA | |
|---|---|---|---|---|---|---|---|
| rate lb/a | rate lb/a | KS | MN | IA | IL | IL | |
| 0.063 | — | 86 | 88 | 52 | 45 | 10 | |
| 0.125 | — | 89 | 99 | 85 | 75 | 10 | |
| 0.179 | — | — | — | 92 | — | — | |
| 0.25 | — | 93 | 99 | 97 | 100 | 42 | |
| — | 0.5 | 90 | 25 | 20 | 42 | 61 | |
| — | 1 | 90 | 56 | 68 | 50 | 53 | |
| | | E | O | E | O | E | O | E | O |
| 0.063 | 0.5 | 99 | 95 | 91 | 99 | 62 | 78 | 68 | 93 | 65 | 88 |
| 0.125 | 0.5 | 99 | 96 | 99 | 99 | 88 | 90 | 86 | 74 | 65 | 72 |
| 0.179 | 0.5 | — | — | — | — | 94 | 95 | — | — | — |
| 0.25 | 0.5 | — | — | — | — | — | — | — | — |

TABLE III-continued

| | | | | | | | | | |
|---|---|---|---|---|---|---|---|---|---|
| 0.063 | 1 | — | — | — | — | — | 50 | 88 | — |
| 0.125 | 1 | — | — | — | — | — | 88 | 100 | — |
| no. of leaves: | | 4–5 | 1–4 | 2–6 | | 4+ | | | — |
| days after treatment that test was rated | | 36 | 42 | 55 | | 14 | | | 42 |

Little or no synergy of ABUTH, CHEAL, POLPY, SO2PT, AMARE or POLPE was observed due to the almost complete control exhibited by NMSC alone at the rates tested. With respect to AMARE, it is noted that this response (relative to the testing summarized in TABLE II) is not contradictory given the difference in hardiness of the European and American Species.

What is claimed is:

1. A synergistic herbicidal composition comprising (a) 2-(2'-nitro-4'-methylsulfonylbenzoyl)-1,3-cyclohexanedione or 2-(2'-nitro-4'-methylsulfonyloxybenzoyl)-1,3-cyclohexanedione; and (b) 2-chloro-4-ethylamino-6-isopropylamino-5-triazine.

2. A composition in accordance with claim 1 wherein the weight ratio of component (a) to component (b) is between about 1:50 and about 1:1.

3. A composition in accordance with claim 1 wherein the weight ratio of component (a) to component (b) is between about 1:40 and about 4:5.

4. A composition in accordance with claim 1 wherein component (a) is 2-(2'-nitro-4'-methylsulfonylbenzoyl)-1,3-cyclohexanedione.

5. A method of controlling undesirable vegetation comprising applying to the locus of such vegetation an effective amount of a synergistic herbicidal composition comprising (a) 2-(2'-nitro-4'-methylsulfonylbenzoyl)-1,3-cyclohexanedione or 2-(2'-nitro-4'-methylsulfonyloxybenzoyl)-1,3-cyclohexanedione; and (b) 2-chloro-4-ethylamino-6-isopropylamino-5-triazine.

6. A method in accordance with claim 5 wherein the weight ratio of component (a) to component (b) is between about 1:50 and about 1:1.

7. A method in accordance with claim 6 wherein the weight ratio of component (a) to component (b) is between about 1:40 and about 4:5.

8. A method in accordance with claim 5 wherein component (a) is 2-(2'-nitro-4'-methylsulfonylbenzoyl)-1,3-cyclohexanedione.

9. A method in accordance with claim 5 wherein said composition is applied postemergence.

* * * * *